United States Patent [19]

Okinoshima

[11] Patent Number: 4,937,364

[45] Date of Patent: Jun. 26, 1990

[54] NOVEL DISILACYCLOHEXANE COMPOUND AND PROCESS FOR PREPARING THE SAME

[75] Inventor: Hiroshige Okinoshima, Annaka, Japan

[73] Assignee: Shin-Etsu Chemical Co., Ltd., Tokyo, Japan

[21] Appl. No.: 440,726

[22] Filed: Nov. 24, 1989

[30] Foreign Application Priority Data

Nov. 26, 1988 [JP] Japan .................. 63-299278

[51] Int. Cl.$^5$ .............................................. C07F 7/08
[52] U.S. Cl. ................................................. 556/406
[58] Field of Search ..................................... 556/406

[56] References Cited

U.S. PATENT DOCUMENTS 3,178,392  4/1965  Kriner .................. 556/406 X
3,465,018  9/1969  Atwell .................. 556/406
4,614,812  9/1986  Schilling ............... 556/406

OTHER PUBLICATIONS

West et al., "S.A.C.S.", 85, pp. 2871–2872, 1963.

*Primary Examiner*—Paul F. Shaver
*Attorney, Agent, or Firm*—Foley & Lardner, Schwartz, Jeffery, Schwaab, Mack, Blumenthal & Evans

[57] ABSTRACT

A disilacyclohexane compound represented by the following general formula (I):

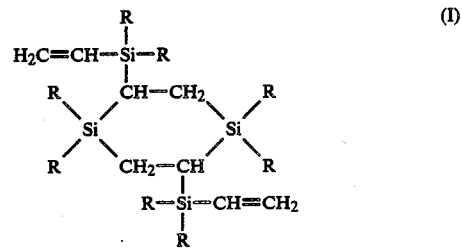

wherein R's may be the same or different and each represent an alkyl group having from 1 to 5 carbon atoms, and the process for preparing the same. This compound is useful as a crosslinking agent in the polymer chemistry and as an intermediate for synthesis of various compounds.

4 Claims, No Drawings

NOVEL DISILACYCLOHEXANE COMPOUND AND PROCESS FOR PREPARING THE SAME

BACKGROUND OF THE INVENTION

1. Field of the Invention

The present invention relates to a novel disilacyclohexane compound useful as a crosslinking agent in polymer chemistry and as an intermediate for synthesis of various compounds, and to a process for preparing the same.

2. Description of the Prior Art

Heretofore, as a reaction accompanied by cleavage of an Si—Si bond of vinyldisilanes, there are known the disproportionation of a monovinyldisilane with dicyclopentane in the presence of a palladium catalyst, represented by the equation:

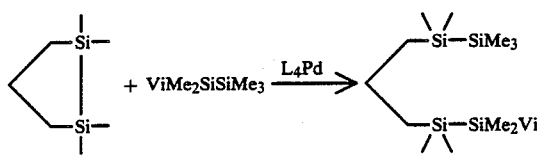

(Advance in Organometallic Chemistry, 19, (1981) 213-255). The present inventors have discovered a novel disilacyclohexane compound prepared by a unique reaction accompanied by the cleavage of the Si—Si bond but unknown heretofore.

SUMMARY OF THE INVENTION

An object of the present invention is to provide a novel disilacyclohexane compound useful as a crosslinking agent for syntheses of polymeric compounds, and as an intermediate for syntheses of a variety of compounds.

Another object of the present invention is to provide a process for preparing said disilacyclohexane compound, which process is accompanied by the cleavage of the Si—Si bond but uses a reaction entirely different from said known reactions.

Thus, the present invention provides a disilacyclohexane compound represented by the following general formula (I):

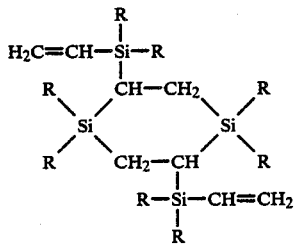

wherein R's may be the same or different and each represent an alkyl group having from 1 to 5 carbon atoms.

The novel disilacyclohexane compound of the present invention is useful as an crosslinking agent for syntheses of polymeric compounds and as an intermediate for syntheses of various polymer compounds or the like by virtue of the two vinyl groups possessed in its molecule.

DETAILED DESCRIPTION OF PREFERRED EMBODIMENTS OF THE PRESENT INVENTION

In the general formula (I), the plural R's may be the same or different and each are a $C_1$ to $C_5$ alkyl group, such as, a methyl group, an ethyl group, a propyl group, a butyl group and the like. Specifically, the alkyl group includes, for example, the methyl group, ethyl group, propyl group and butyl group, and substituted alkyl groups formed by substitution of part or all of the hydrogen atoms of said alkyl groups with a halogen atom such as a fluorine atom, chlorine atom or iodine atom, an alkoxyl group, a silyl group or siloxy group.

The disilacyclohexane compound represented by said general formula (I) can be prepared as the dimer of the 1,2-vinyldisilane compound having the general formula (II):

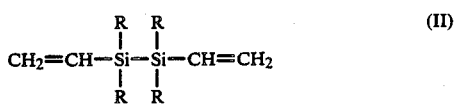

wherein R's are the same as defined in respect of said general formula (I),
by reacting said 1,2-divinyldisilane compound in the presence of a platinum family metal catalyst. The 1,2-divinyldisilane compound includes, for example, 1,2-divinyl-tetramethyldisilane, 1,2-divinyl-1,2-diethyl-1,2-dimethyldisilane, and 1,2-divinyl-1,2-bis(trimethylsilylmethyl)-1,2-dimethyldisilane.

The platinum family metal catalyst used in the above preparation is not limited, and includes a platinum, palladium or rhodium catalyst. Preferred are platinum catalysts, for example, chloroplatinic acid, an alcohol-modified chloroplatinic acid, a platinum-vinylsiloxane, a platinum black, a complex of a chloroplatinic acid with an olefin or aldehyde. Particularly preferred are the chloroplatinic acid, alcohol-modified chloroplatinic acid, and platinum-vinylsiloxane in view of their high activity. The platinum family metal catalyst is normally used in an amount of about 1 to 100 ppm in terms of platinum based on the whole reaction mixture. If the amount of the platinum family metal catalyst is too small, the reaction proceed at a low rate and ineffectively. If the amount thereof is too large, on the other hand, a variety of side reactions may occur, resulting in a low yield of the disilacyclohexane compound of the general formula (I).

The above preparation is usually carried out in an organic solvent, typical examples of which include aliphatic hydrocarbons such as n-pentane, n-hexane, n-heptane and n-octane; aromatic hydrocarbons such as benzene, toluene and xylene; ethers such as tetrahydrofuran, dioxane and dibutyl ether. The amount of the organic solvent used is not particularly limited, and preferably it is used in an amount 2 to 5 times by weight that of the starting material, i.e., said 1,2-divinyldisilane compound of the general formula (II). If the amount of the organic solvent is too small, the disilacyclohexane compound is produced in a low yield. If the amount of the organic solvent is too large, the reaction rate become low, so that the reaction takes a long time before completion.

The reaction is carried out normally at about 50° to 200° C., preferably at 80° to 140° C. The reaction usually completes within from 2 to 5 hours. If the reaction temperature is too low, the reaction unpractically takes a long time before completion. If the reaction temperature is too high, the disilacyclohexane of the general formula (I) produced may polymerize, resulting in a low yield.

The reaction is preferably carried out in a dry inert atmosphere, such as a nitrogen or argon atmosphere.

According to the above process, the disilacyclohexane compound can be prepared with ease and in a good yield.

EXAMPLES

The present invention is now described in more detail with reference to working examples which are nonlimitative to the scope of the present invention. In the description below, part(s) means part(s) by weight unless otherwise noted.

EXAMPLE 1

A reaction vessel of which the inside atmosphere was previously replaced with nitrogen gas was charged with 5 parts of 1,2-divinyltetramethyldisilane, 20 parts of toluene and 0.025 part of a platinum-vinylsiloxane (platinum content: 1%). The contents were then made a uniform solution, which was heated at 110° C. for 5 hours. The resulting reaction mixture was analyzed by gas chromatography, indicating that the starting material 1,2-divinyltetramethyldisilane completely disappeared and two kinds of compounds formed in almost equal amounts. The reaction mixture was subjected to flash distillation under vacuum; a mixture containing the two kinds of compounds was separated. The mixture containing the product compounds was subjected to preparative gas chromatography (Column: inner diameter 10 mm, length 3 m; packing material; SE-30 in an amount of 5% loading by weight carried by Uniport HP), and thereby separated to every peak component. Each isolated component was subjected to analyses by NMR spectroscopy, GC/MS and elemental analysis. From the data obtained, the component having the longest retention time among the separated peak components was found to be 1,1,4,4-tetramethyl-2,5-bis(-vinyldimethylsilyl)-1,4-disilacyclohexane (hereinafter, referred to Compound (i)). Yield: 50%. The results of the analyses are given below.

NMR Spectrum (CCl$_4$, external standard: tetramethylsilane) δ: −0.04 to −0.42 (m, 2H) 0.02 (s, 24H) 0.40 to 1.16 (m, 4H) 5.56 to 6.68 (m, 6H).

GC/MS: 340 (M+).

Elemental analysis:

|  | C | H | Si |
|---|---|---|---|
| Found: | 56.29 | 10.64 | 32.67 |
| Calculated:* | 56.39 | 10.65 | 32.96 |

*as C$_{16}$H$_{36}$Si$_4$

EXAMPLE 2

The procedure in Example 1 was repeated except that a chloroplatinic acid (H$_2$PtCl$_6$.H$_2$O) solution in 2-ethylhexanol in a concentration of 1% in terms of platinum was used as the catalyst in place of the platinum-vinylsiloxane. The same results as in Example 1 were obtained.

EXAMPLE 3

The procedure in Example 1 was repeated except that xylene was used in place of the toluene. The same substance as that obtained in Example 1 was obtained. Further, in the case where dioxane was used as the solvent in place of the toluene, the same substance as that obtained in Example was also obtained.

EXAMPLE 4

The procedure in Example 1 was repeated except that xylene was used as the solvent in place of the toluene, and the reaction was carried out at 140° C. instead of 110° C. Compound (i) was obtained in a 30% yield. The other products yielded in slight amounts.

EXAMPLE 5

The procedure in Example 1 was repeated except that the reaction was carried out for 48 hours instead of 5 hours. The resulting products were subjected to gas chromatography; hence only the peak due to Compound (i) was observed. Yield: 45%.

We claim:

1. A disilacyclohexane compound represented by the following general formula (I):

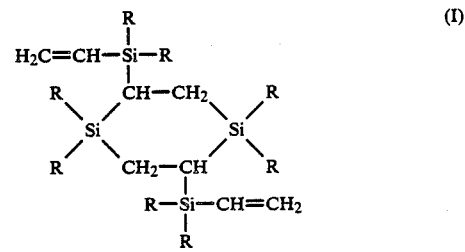

wherein R's may be the same or different and each represent an alkyl group having from 1 to 5 carbon atoms.

2. The compound according to claim 1, wherein R in the general formula (I) is at least one member selected from the group consisting of a methyl group, an ethyl group, a propyl group and a butyl group.

3. A process for preparing the disilacyclohexane compound represented by the general formula (I):

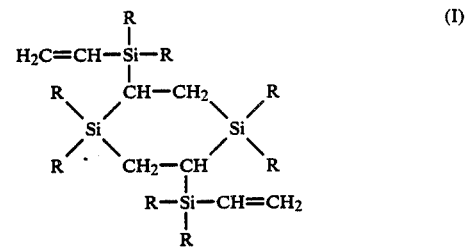

wherein R's may be the same or different and each represent an alkyl group having from 1 to 5 carbon atoms, comprising the step of reacting a 1,2-vinyldisilane compound having the general formula (II):

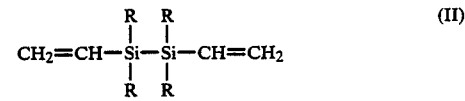

wherein R's are the same as defined in respect of the general formula (I), in the presence of a platinum family metal catalyst.

4. The process according to claim 3, wherein R in the general formula (I) and (II) is at least one member selected from the group consisting of a methyl group, an ethyl group, a propyl group and butyl group.

* * * * *